United States Patent [19]

Welch et al.

[11] Patent Number: 4,886,354
[45] Date of Patent: Dec. 12, 1989

[54] METHOD AND APPARATUS FOR MEASURING CRYSTAL FORMATION

[75] Inventors: Gary E. Welch; Marvin R. Appel, both of Ponca City; Jerry R. Bittle, Blackwell, all of Okla.

[73] Assignee: Conoco Inc., Ponca City, Okla.

[21] Appl. No.: 191,306

[22] Filed: May 6, 1988

[51] Int. Cl.$^4$ ............... G01N 33/26; G01N 21/21
[52] U.S. Cl. .................... 356/70; 250/225; 356/364; 356/366
[58] Field of Search ............ 356/70, 364–370, 356/410; 250/225

[56] References Cited

U.S. PATENT DOCUMENTS

| | | | |
|---|---|---|---|
| 2,668,470 | 2/1954 | Fischer | 356/367 |
| 2,852,693 | 9/1958 | Hughes et al. | 356/446 |
| 3,941,482 | 3/1976 | Schneider | 356/365 |
| 4,113,384 | 9/1978 | Lauer et al. | 356/70 |
| 4,201,471 | 5/1980 | Pitt et al. | 356/70 |
| 4,529,306 | 7/1985 | Kilham et al. | 356/338 X |
| 4,572,676 | 2/1986 | Biermans et al. | 356/366 X |
| 4,795,262 | 1/1989 | Morris et al. | 356/410 X |

FOREIGN PATENT DOCUMENTS 1113293 5/1968 United Kingdom ............... 356/364

*Primary Examiner*—Vincent P. McGraw
*Attorney, Agent, or Firm*—Cleveland R. Williams

[57] ABSTRACT

Apparatus for measuring the formation of crystals in a flowing liquid using a flow way that receives a flow of the liquid therethrough; wherein, the flow way includes an optical means and access for illuminating the liquid with a beam of polarized light and then imaging the illuminated liquid to qualitatively ascertain the rate and type of crystal formation within the liquid.

3 Claims, 2 Drawing Sheets

METHOD AND APPARATUS FOR MEASURING CRYSTAL FORMATION

BACKGROUND OF THE INVENTION

1. Field of the Invention.

This invention relates generally to methods and apparatus for measuring the formation of crystals in a flowing liquid, and more particularly, but not by way of limitation, to methods and apparatus for measuring the formation of wax crystals in cooled crude oil.

2. Description of the Prior Art.

The presence of waxes in crude oil poses significant problems, particularly in the transport of crude oil in a pipeline. Oil produced from offshore formations is recovered initially at a temperature in excess of the melting point of such waxes, so that initially at least the waxes are in a molten, liquid state. As this oil is transported through the pipeline from an offshore platform, however, the oil is cooled by heat transfer with the surrounding sea. Eventually the waxes present in the oil begin to solidify and form crystals. If for any reason the pumping of the oil through the pipeline is stopped, the wax crystals thus formed can gather and form a solid block to further movement of the oil through the pipeline. Substances known as pour point depressants have therefore been developed to inhibit the tendency of the waxes to solidify at the temperatures experienced in the pipeline.

A patent to Fischer, U.S. Pat. No. 2,668,470, discloses a method and apparatus for determining by electrooptical analysis the percentage of crystal solids formed from or in liquids at reduced temperatures, with particular application to analytical determination of paraffin wax in mineral oils and wax cakes upon elimination of turbidity. A filtered and polarized light beam from a rheostatted light source is passed through a crystallizing unit for a predetermined time interval, with the intensity of the light beam being gradually increased over the interval to record a mean optical activity for crystals formed in the crystallizing unit.

The crystallizing unit provides a crystal forming space in an otherwise insulated conduit containing a flow of the liquid, which space is formed by placing a series of uniformly spaced transparent plates between a pair of glass plates. Crystals are formed in and removed from the unit by ejecting at various times in the cycle of operation flows of cooling and heating air, respectively, against the unit. An insulated bypass is provided for diverting the flow of liquid away from the unit when the crystals are formed.

The mean optical activity over the predetermined interval of a system of unknown wax composition is compared with a set of curves produced for different wax compositions in the liquid. An indication of the percentage of crystal solids which are formed from or in the unknown system generally at reduced temperatures can be gained from such a comparison.

The device disclosed in the patent to Fischer does not, however, provide means for qualitatively monitoring the formation of crystals in a flowing liquid or for a comparative study of the rates of formation of such crystals in different systems and under a variety of conditions. Tests with various pour point depressants have indicated significant differences in the structure of wax crystals formed under identical conditions but for the presence of different pour point depressants. Tests have further demonstrated the impact of such differences on the tendency of such crystals to form effective blocks to flow in a pipeline at reduced temperatures.

An apparatus which provides means for qualitatively monitoring the formation of crystals in a flowing liquid, and/or for a comparative study of the rates of formation in different systems and under a variety of conditions, could be an especially effective tool in evaluating and suggesting means for combating the formation of an effective block of wax crystals in a pipeline.

It is therefore an object of this invention to provide for the qualitative monitoring of the formation of crystals in a flowing liquid.

It is another object of this invention to provide for such monitoring in a laboratory scale simulation of actual pipeline conditions.

It is a further object of this invention to provide an apparatus and method for evaluating the effectiveness of pour point depressants in inhibiting the formation of wax crystals in a pipeline.

It is a still further object of this invention to provide such an apparatus and method for evaluating the effectiveness of pour point depressants in terms of their effect on the structure and rate of formation of wax crystals in a pipeline.

Other objects and advantages will be apparent from a consideration of the following description, the appended claims, and the accompanying drawings.

SUMMARY OF THE INVENTION

The present invention overcomes the above-noted and other shortcomings of the prior art by providing an improved apparatus and method for monitoring the formation of crystals in a flowing liquid.

The apparatus comprises a conduit for channeling a flow of the liquid, illuminating means for directing a beam of polarized light through the flow of liquid, and qualitative monitoring means for permitting the qualitative monitoring of the formation of crystals in the liquid. The qualitative monitoring means of the apparatus of the present invention includes a transparent window defined in a wall of the conduit, with camera means associated with the window for receiving an image therefrom. The qualitative monitoring means includes also a monitor operably associated with the camera means for concurrently displaying the image and recorder means operably associated with the camera means for recording the image received by the camera means. Temperature control means is provided for controlling the temperature of the flow of liquid through the conduit proximate the transparent window.

The method of using an apparatus which has a light transmissive window defined in a wall thereof and a transparent window defined in a wall thereof comprises directing a beam of polarized light through the light transmissive window and receiving an image from the transparent window. The method of using such an apparatus includes also the steps of continuously monitoring the image and of controlling the temperature of the flowing liquid proximate the transparent window.

DETAILED DESCRIPTION OF THE PREFERRED EMBODIMENT

Figure 1:
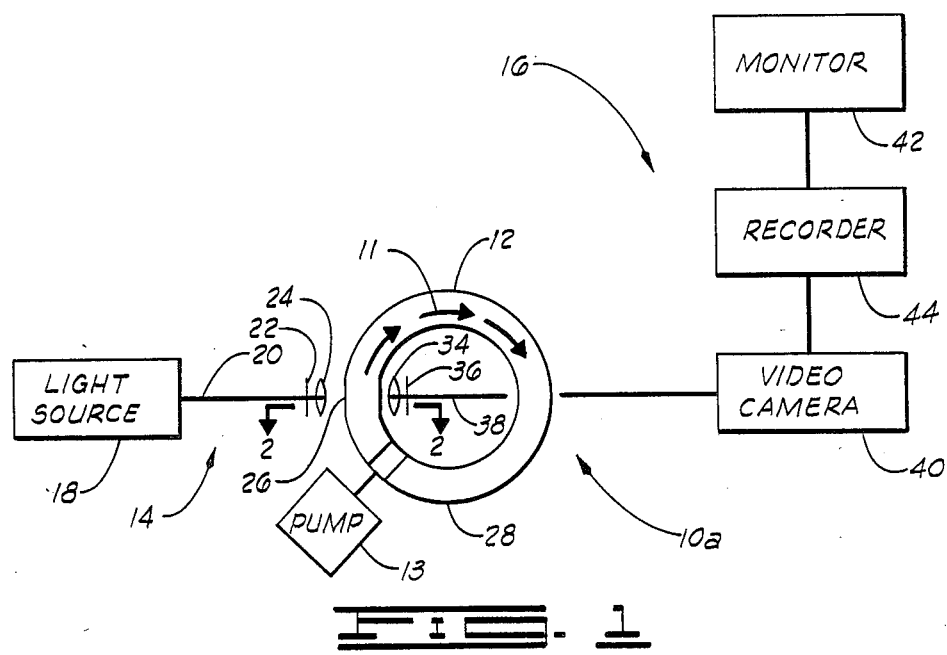
FIG. 1 is a schematic of a first embodiment of the apparatus of the present invention.
Figure 4:
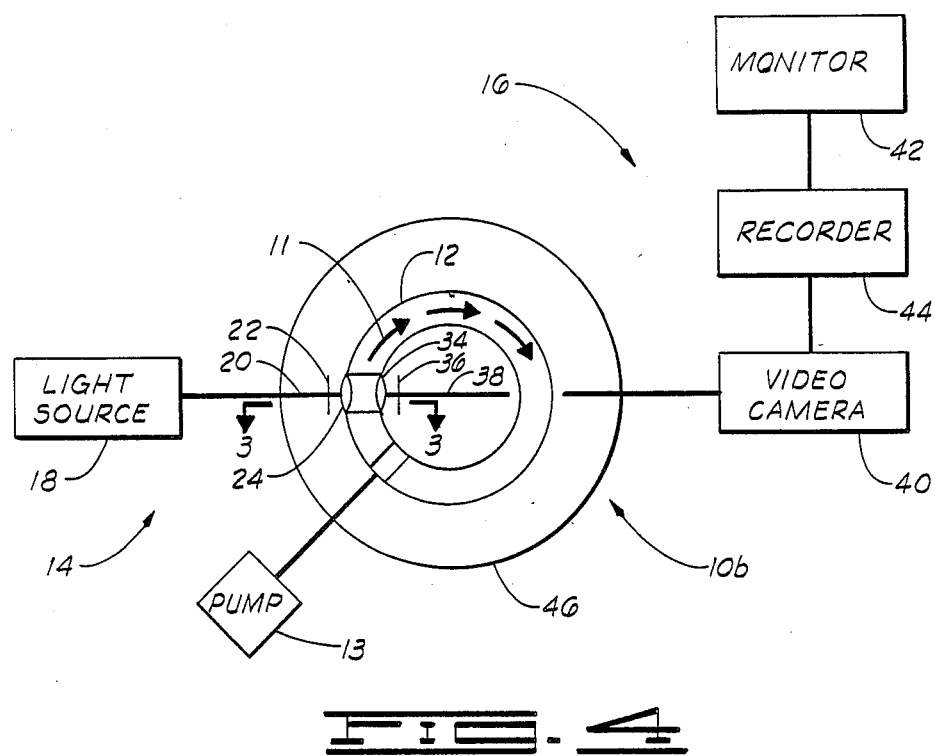
FIG. 4 is a schematic view of the second embodiment of the apparatus of the present invention.

Referring now to the drawings, and more particularly to FIGS. 1 and 4, alternative embodiments of the apparatus of the present invention are shown and generally designated 10a and 10b, respectively.

In FIG. 1, a first embodiment 10a of the apparatus comprises a conduit for channeling a flow of a liquid, herein circuit means such as a piping loop 12 for providing a substantially unrestricted flow path for a volume of liquid introduced therein by conventional means known to the art. A peristaltic pump 13 is associated with the piping loop 12 for pumping the volume of liquid contained therein through the piping loop 12. A peristaltic pump is used to minimize shear degradation during the pumping process of any crystals formed in the liquid 11 and of any pour point depressant or depressants present in the system being tested.

The first embodiment 10a further comprises illuminating means 14 for directing a beam of polarized light through the flow of the liquid 11, and qualitative measuring means 16 operably associated with the illuminating means 14 for permitting the qualitative monitoring of the formation of crystals in the liquid within the piping loop 12.

Figures 2, 3:
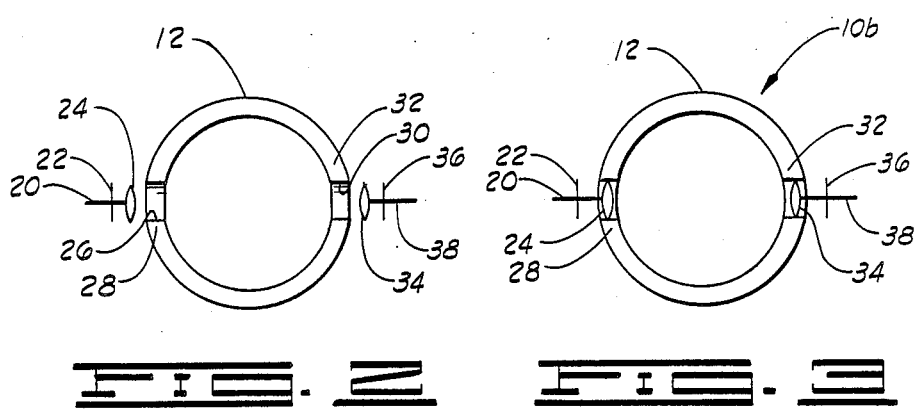
FIG. 2 is a cross-sectional view of the conduit of the first embodiment, taken along lines 2—2 in FIG. 1.
FIG. 3 is a cross-sectional view of the conduit of the second embodiment of the apparatus of the present invention, taken along the lines 3—3 in FIG. 4.

Illuminating means 14 comprises a light source 18, a light guide 20 for guiding the light produced by the light source 18, a polarizing filter 22 for polarizing the light thus guided, and a condensing lens 24 for forming a beam of polarized light. The light guide 20 may be composed of a plurality of light-carrying glass fibers or may comprise merely a single Lucite ® brand plastic rod. The condensing lens 24 is positioned for directing the beam of light through a light transmissive window 26 defined in a wall 28 of the loop 12, as may be seen by reference to FIG. 2. Referring to FIGS. 1 and 2, the qualitative monitoring means 16 comprises a transparent window 30 defined in a wall 32 of the loop 12 and which opposes light transmissive window 26. In the first embodiment 10a, the transparent window 30 is aligned with light transmissive window 26 such that the beam of polarized light directed through the light transmissive window passes through transparent window 30 also.

The light thus produced and directed is made to pass through a diverging lens 34 and a second polarizing filter 36. The light is guided by a light guide 38 to camera means, such as a video camera 40, thereby associated with transparent window 30 for receiving an image from the transparent window 30. A monitor 42 and recorder means such as a video recorder 44 are operably associated with the video camera 40 for concurrently displaying and recording, respectively, the image so received.

Referring now to FIGS. 3 and 4, a second, preferred embodiment 10b of the apparatus is depicted. Specifically referring to FIG. 3, it can be seen that the condensing lens 24 of the preferred embodiment 10b comprises a second, transparent window defined in the wall 28 of the piping loop 12, thereby replacing the two element construction involving the condensing lens 24 and the light transmissive window 26 of the first embodiment 10a (FIG. 2). Similarly, the diverging lens 34 of the preferred embodiment 10b comprises a first transparent window defined in the wall 32 of the piping loop 12 so that the lens 34 opposes the lens 24. The two element construction of the first embodiment 10a involving the diverging lens 24 and the transparent window 30 (FIG. 2) is thus condensed into the single element of the diverging lens 34 of the second, preferred embodiment 10b.

The second, preferred embodiment 10b of the apparatus of the present invention further comprises temperature control means, such as the constant temperature bath 46, for substantially uniformly controlling the temperature of the flow of liquid 11 through the piping loop 12 and for thus controlling the temperature of the liquid 11 proximate the transparent window 30 or the diverging lens 34. Controlling the temperature of the liquid 11 proximate the transparent window 30 or the diverging lens 34 only, and thus proximate only the monitored portion of the piping loop 12, enables a study of the formation and structure of crystals in a given system at a given temperature. The conditions prevailing for the given system at a certain distance from the platform in a crude oil pipeline proceeding from an offshore platform, after the requisite amount of cooling has occurred, may thus be approximated.

Providing temperature control means for substantially uniformly controlling the temperature of the volume of liquid 11 flowing in the piping loop 12, as by immersion of the piping loop 12 in the constant temperature bath 46 schematically depicted in FIG. 4, permits the monitoring of the rates of formation of crystals in various systems at particular temperatures. Controlling the temperature of the liquid 11 proximate only the monitored portion of the piping loop 12, as could be accomplished by, for example, immersion of only that portion of the piping loop 12 in the constant temperature bath 46, assures only the temperature of the system over a narrow time span except at extremely low flow rates. The crystals formed over the time span could be altered upon passing from the controlled region of the piping loop 12, so that prolonged study of the accumulation of such crystals at a given temperature and the rate of accumulation of such crystals could be made difficult.

Conversely, however, a quick study of the effects of temperature on the structure of crystals formed in a given system could be accomplished more efficiently by controlling the temperature of the liquid 11 proximate the monitored portion of the piping loop 12, as opposed to changing the temperature of the constant temperature bath 46 and allowing the bath 46 to reach thermal equilibrium at the new temperature. The particular temperature control means chosen may accordingly vary depending on the intended use of the apparatus.

In using the second, preferred embodiment 10b of the apparatus, wherein the piping loop 12 is immersed in the constant temperature bath 46, it will be necessary to adjust for the interference of the bath liquid with the images received by the video camera 40. Water is a convenient choice for a bath liquid because it maintains an essentially constant index of refractivity over the temperature ranges encountered by oil in a pipeline from an offshore platform. This constant level of refraction can be accommodated by an appropriate machining of the lenses of the apparatus to produce images for the monitor 42 and the video recorder 44 that exhibit a minimum of distortion due to the bath liquid's presence.

It is contemplated that, from time to time, it may be desirable to stop the peristaltic pump 13 from operating, and to thereby simulate the effects of a cessation of pumping in a pipeline. The present apparatus accordingly provides means for continuously monitoring the formation of crystals into a block to further flow through the piping loop 12, and for monitoring the effectiveness of various pour point depressants and depressant combinations at various temperatures in inhibiting the formation of an effective block. An indication may be garnered from these observations also as to the length of time available for repair and restoration of flow for various systems under pipeline conditions.

While a preferred embodiment of the invention has been described for the purpose of this disclosure, numerous changes in the construction and arrangement of parts can be made by those skilled in the art, which changes are encompassed within the spirit of this invention, as defined by the appended claims.

What is claimed is:

1. An apparatus for measuring the formation or crystals in a flowing liquid, comprising:
    a piping loop having first and second opposing transparent windows defined therein;
    a peristaltic pump associated with said piping loop for pumping a volume of said liquid through said piping loop;
    illuminating means for directing a beam of polarized light through said first and second opposing transparent windows, positioned adjacent said second transparent window;
    a video camera positioned adjacent said first transparent window for receiving an image therefrom; and
    a constant temperature bath for immersing said piping loop therein.

2. The apparatus as defined in claim 1, further comprising a recorder operably associated with said video camera for recording said image.

3. The apparatus as defined in claim 1, further comprising a monitor operably associated with said video camera for concurrently displaying said image.